United States Patent [19]

Gottlieb

[11] Patent Number: 4,699,898

[45] Date of Patent: Oct. 13, 1987

[54] TRIPEPTIDES AFFECTING IMMUNE RESPONSE

[75] Inventor: A. Arthur Gottlieb, New Orleans, La.

[73] Assignee: Imreg, Inc., New Orleans, La.

[21] Appl. No.: 813,632

[22] Filed: Dec. 26, 1985

[51] Int. Cl.$^4$ ............................................. A61K 37/02
[52] U.S. Cl. ....................................... 514/18; 424/85; 424/88
[58] Field of Search .................... 424/85, 88; 530/331; 514/18

[56] References Cited

U.S. PATENT DOCUMENTS 4,426,324  1/1984  Meienhofer .......................... 530/331
4,616,079 10/1986  Gottlieb ................................ 424/85

OTHER PUBLICATIONS

Biochimica et Biophysica Acta, 657 (1981), 122–127.

Primary Examiner—Delbert K. Phillips
Attorney, Agent, or Firm—Richard H. Stern

[57] ABSTRACT

A tripeptide and derivatives thereof are described that amplify mammalian immune response. A purification process, methods of using, and pharmaceutical compositions for using the product are disclosed.

22 Claims, No Drawings

TRIPEPTIDES AFFECTING IMMUNE RESPONSE

BACKGROUND OF THE INVENTION

Field of the Invention

The present invention relates to peptides having an influence on human and animal immune response, particularly the amplification of immune response, to compositions containing such peptides, and to methods of purifying and preparing such peptides in a pharmaceutically acceptable form. The invention also includes the use of such peptides to influence immune response.

In a number of diseases or other pathological conditions, the immune system response of the human or animal subject is depressed. As a result the subject becomes more susceptible to opportunistic infections, malignancies, or other pathological conditions against which a normal immune system would have protected the subject. Among the pathological conditions that depress the immune system are Acquired Immune Deficiency Syndrome (AIDS) and AIDS-related complex (ARC). Chemotherapy and aging are also associated with immune deficiency.

The inventor has discovered that leukocyte dialysates contain immunomodulators, which are materials or substances having therapeutic utility, as described in detail in U.S. Pat. No. 4,468,379. The U.S. Pat. No. 4,468,379 discloses a process for extracting such substances and methods of using them, as well as compositions containing immunomodulators. Other processes are disclosed in pending U.S. application Ser. No. 643,724. In general, immunomodulators have the property of modulating the response of a subject's immune system to antigens to which the subject's system has been previously exposed. Amplifier immunomodulators, or amplifiers, amplify or accelerate immune response. Suppressor immunomodulators, or suppressors, suppress immune response. The U.S. Pat. No. 4,468,379 and the U.S. application Ser. No. 643,724 disclose materials extracted from human and animal leukocyte preparations, with molecular weight (M.W.) generally below 3500. (An exception is a material designated L-suppressor, which appears to have a much greater M.W.) The chemical structure of these materials is not disclosed, although various properties of the materials are disclosed (such as elutability characteristics.)

It is not known at this time whether the immunomodulating properties of the materials described in the U.S. Pat. No. 4,468,379 and the U.S. application Ser. No. 643,724 are attributable to their containing molecules with the structures described hereinafter. It is the inventor's present hypothesis that the molecules and structures described hereinafter are a portion of the immunoamplifiers described in the U.S. Pat. No. 4,468,379 and the U.S. application Ser. No. 643,724, but not the entire active portion thereof.

A general discussion of the same field as that of this invention may be found in Kisfaludy et al. U.S. Pat. No. 4,428,938, "Peptides affecting the immune regulation and a process for their preparation", issued Jan. 31, 1984. That patent mainly concerns peptides of the form X-Arg-Lys-Y, where X may be null or Glp, and Y may be Asp, Asp plus other aminos, or several aminos terminated by Val. The U.S. Pat. No. 4,428,938 does not disclose peptides consisting of or containing the sequence Tyr-Gly-Gly. The U.S. Pat. No. 4,428,938 also covers salts, amides, lower alkyl esters and protected derivatives of the designated peptides.

Meienhofer U.S. Pat. No. 4,426,324, "Immunopotentiating peptides," issued Jan. 17, 1984, is also directed to the field of this invention. It discloses peptides of the form X-Glu-Asn-OH, and claims such peptides together with the pharmaceutically acceptable salts thereof. The U.S. Pat. No. 4,426,324 also does not deal with peptides consisting of or containing a Tyr-Gly-Gly triplet.

Other Background

The Tyr-Gly-Gly triplet of amino acids exists as a commercial product, with contaminants, however, that appear to make it unsuitable for administration to human or animal subjects. The triplet occurs also in opioid peptide chains disclosed in the literature. (Opioid peptides are so-called because of their ability to bind to receptors which also bind morphine and other narcotic substances.) For example, alpha-endorphin is a 16 amino acid peptide molecule containing the sequence Tyr-Gly-Gly. Beta-endorphin is a 31 amino acid peptide molecule containing that sequence, and gamma-endorphin is a 17 amino acid peptide molecule containing that sequence. Also, Met-enkephalin and Leu-enkephalin are pentapeptides that contain Tyr-Gly-Gly sequences. As pointed out in Wybran, "Enkephalins and endorphins as modifiers of the immune system: present and future," in 44 Federation Proc. 92–94 (1985), it has been observed that the five foregoing opioid peptide molecules can influence several immune system functions, suggesting that T and B lymphocytes have surface receptors for such endorphins and enkephalins, and that endorphins and enkephalins may qualify as immunomodulators with therapeutic utility. Similar observations are found in Wybran's abstract, "Enkephalins are likely to be lymphocyte activation molecules," Abstracts, Eur. Cong. of Immunology, Jerusalem, September 1985. Wybran does not point out, however, in connection with the latter suggestion, the severe regulatory difficulties that would attend clinical testing and regulatory approval for the use of substances closely related to presently controlled substances, the marketing of which is unlawful except under very stringent legal controls.

Similar work is discussed in Plotnikoff et al., "Enkephalins: immunomodulators," in 44 Federation Proc. 118–22 (1985). This paper and Wybran, Federation Proc., supra, list other references in the field. It is believed that no such reference, however, refers to Tyr-Gly-Gly per se or simple derivatives of that triplet. Instead, it is believed that all references have been to longer peptide opiode molecules that contain that triplet among many other amino acids.

Finally, Plotnikoff, U.S. Pat. No. 4,537,878, "Process for using endogenous enkephalins and endorphins to stimulate the immune system," issued Aug. 27, 1985, is also directed to the field of this invention. It discloses that enkephalins and endorphins may be used to stimulate immune system response, in terms of NK cell activity and increase in active T-cell rosettes. The U.S. Pat. No. 4,537,878 does not deal with peptides consisting of a Tyr-Gly-Gly triplet without other amino acids as part of the sequence.

Rather, it is directed to a large number of longer peptides, the smallest two of which, Met and Leu enkephalins, are pentapeptides (TGG-Phe-Met and TGG-Phe-Leu), and the rest of which are one or the other of those pentapeptides as part of a sequence of one to five additional amino acid groups. In addition, the U.S. Pat.

No. 4,537,878 does not disclose effects on cell-mediated immunity related to T helper cells, for example in terms of increased delayed hypersensitivity (DH) reaction or correction of immune defects. The U.S. Pat. No. 4,537,878 proposes a hypothesis that enkephalins activate T cells to release interleukin-2, but it does not present data to confirm this hypothesis.

As indicated above, one of the problems with use of the opioid peptides is their close relation to already controlled substances. This relationship, and the known mind-affecting properties of enkephalins and endorphins, creates a strong presumption that any immunoregulatory effects of such products as therapeutic agents is likely to be accompanied by side effects on the central nervous system, some of which may be like that of a narcotic substance. It would therefore be desirable to discover molecules with similar activity that were not so closely related to controlled substances, because that would avoid very severe practical problems, including potential problems with FDA and DEA.

It should be noted, as it is noted in the U.S. Pat. No. 4,426,324, that it is known in the peptide art that deletion of even one amino acid from the sequence of a biologically active peptide can result in the loss of biological activity. The U.S. Pat. No. 4,426,324 therefore points out that it is unexpected that a short peptide sequence within a longer peptide sequence will display similar biological activity to that of the long sequence. Thus, it is not to be expected that a triplet within one of the opioid peptides will display immunomodulatory activity similar to that of the whole opioid peptide.

SUMMARY OF THE PRESENT INVENTION

The inventor has discovered that the Tyr-Gly-Gly triplet, without the remainder of the opioide peptides hitherto discussed, is able to cause immunomodulating effects of the amplifier type. Consequently, use of products based on that triplet can provide desirable immunoregulatory properties provided by the above-discussed opioid peptides with two significant additional benefits. First, Tyr-Gly-Gly is neither a controlled substance nor closely akin to one. Second, it is commercially available, albeit in an impure form that is not pharmaceutically acceptable. A further aspect of the present invention, therefore, is to provide a feasible system for removing medically unacceptable substances from commercial Tyr-Gly-Gly.

DETAILED DESCRIPTION OF PREFERRED EMBODIMENT

I. Purification of TGG

Commercially available tripeptide Tyr-Gly-Gly (TGG), such as that sold by Sigma Chemicals Inc. (St. Louis, Mo.), contains various undefined substances that may harm a human or animal subject. Their presence in a pharmaceutical preparation containing TGG is therefore not medically acceptable.

EXAMPLE 1—PURIFICATION PROCEDURE FOR TGG 1 microgram of TGG (Sigma Chemicals Inc., St. Louis, Mo.) contained in 1 microliter of normal saline is mixed with 99 microliters of 0.05% trifluoroacetic acid in water. 50 microliters of this mixture are injected into a reverse phase HPLC analytic column (ODS Analytic Column, duPont-Zorbax, 4.6 mm×25 cm) and eluted with the following combination of linear gradients:

| Solvent A = 100% acetonitrile Solvent B = 0.05% trifluoroacetic acid in water | | |
|---|---|---|
| Time | % A | to % B |
| Init. | 0 | 100 |
| 15 min. | 6 | 94 |
| 45 min. | 40 | 60 |
| 50 min. (end) | 0 | 100 |

The elution curve absorbance at 210 A (0.05 O.D. units full scale) shows a sharp and narrow peak, much higher than any other peaks, at approximately 21.5 to 22.7 minutes. This elutant is TGG, substantially free of contaminants.

The material associated with the peak is recovered, lyophilized, and made up in sterile normal saline.

It should be noted that elution time tends to decrease with the increasing age of the column (i.e., increased number of uses). Also, adding further solutes (moieties) tends to decrease elution time. The 22.7 min figure above is for a fresh column.

II. In vivo tests of TGG as amplifier

Purified TGG of Example 1, supra, was dissolved into sterile saline, to a final concentration of $3 \times 10^{-13}$M. That preparation was designated as Preparation A. Further 1:10 successive dilutions were prepared from Preparation A, resulting in Preparations B, C, and D, with the following molar concentrations of TGG:

| A | B | C | D |
|---|---|---|---|
| $3 \times 10^{-13}$ | $3 \times 10^{-14}$ | $3 \times 10^{-15}$ | $3 \times 10^{-16}$ |

Samples of 0.1 ml each were injected intradermally into a recipient test subject (human), in combination with an antigen to which the recipient had previously been shown to be sensitive. The antigen employed was 0.05 ml of tetanus toxoid (1/20 dilution of standard fluid tetanus toxoid, Squibb/Connaught). In addition, the same amount of tetanus toxoid antigen was injected in combination with 0.1 ml of normal sterile saline without any TGG, as a control (Preparation E). After 6, 10.5, and 23 hours, respectively, the injection sites were examined and the dimensions of the lesions were tabulated. The results of this testing are shown in Table 1. (The test subject, an adult human male, weighed approximately 70 kg.)

TABLE 1

| Dermal reaction to antigen, with and without TGG (Size of lesion in mm × mm) | | | | |
|---|---|---|---|---|
| Preparation | Conc. | 6 hrs. | 10.5 hrs. | 23 hrs. |
| A | $3 \times 10^{-13}$ M | 12 × 10 | 15 × 17 | 15 × 15 |
| B | $3 \times 10^{-14}$ M | 14 × 12 | 15 × 18 | 16 × 18 |
| C | $3 \times 10^{-15}$ M | 17 × 18 | 20 × 22 | 18 × 17 |
| D | $3 \times 10^{-16}$ M | 12 × 11 | 14 × 14 | 10 × 11 |
| E | saline control | 7 × 7 | 9 × 9 | 13 × 12 |

As an additional control, 0.1 ml of TGG, Preparation C, above, was injected into the test subject without antigen. No reaction was observed over a 48 hour period.

It is seen from Table 1 that 0.1 ml of 3 femtomolar solution (1 femtomole = $1 \times 10^{-15}$ GMW; 1 femtomolar = $1 \times 10^{-15}$M; both are abbreviated hereinafter as 1 fM) at 10.5 hours, which is a total dosage amount of $3 \times 10^{-19}$ moles, produces the maximum response. Dosages of 0.1 ml of 30 fM and 300 fM solutions produce less effect than 0.1 ml of 3 fM solution, because increasing the dosage beyond the optimum produces a paradoxical effect, viz., lessened immune reaction with increasing amplifier dosage. Similar effects are noted in the inventor's U.S. Pat. No. 4,468,379. It is also seen from Table 1 that decreasing the dosage from 3 fM to 0.3 fM produces less lesion, since 3 fM is approximately optimum for maximum immune effect in this test.

The great sensitivity of the human immune system to TGG is shown by these tests. A dose of 0.1 ml of 3 fM solution of a therapeutic agent is a very minute dose (0.0003 femtomoles). One femtomole of TGG is approximately $277 \times 10^{-9}$ micrograms. One picomole ($=1 \times 10^{-12}$ GMW) of TGG is approximately $277 \times 10^{-6}$ micrograms. Examination of references such as the Physicians' Desk Reference (PDR) shows that ordinary therapeutic dosages of pharmaceuticals are typically vastly in excess of a femtomole or a picomole.

III. In vitro tests of TGG

It is generally considered that one index of immune system activity is ability to generate interleukin-II (IL-2) in vitro in response to mitogen stimulation. Tests of TGG's ability to stimulate in vitro IL-2 production in lymphocytes of normal test subjects patients were therefore performed. The tests typically indicated an optimum concentration of TGG for IL-2 stimulation, such that at concentration of TGG greater or less than the optimum concentration the production of IL-2 in response to mitogen is not as great as it is at the optimum. In Table 2 there are shown for two normal subjects their respective highest ratios of IL-2 production in response to the mitogen PHA (Wellcome Reagents HA 16), with and without TGG added to the sample. (The methodology of the tests generally follows that of the literature.)

TABLE 2

Ratio of PHA-stimulated IL-2 Production, With and Without TGG Added, in Normal Subjects

| Subject | Highest ratio |
|---------|---------------|
| #1      | 1.4           |
| #2      | 2.55          |

The tests generally indicate an enhancement of IL-2 optimal production as a result of adding TGG. TGG thus appears to be a potent agent for stimulating or amplifying immune response.

IV. Tests of TGG derivatives

It is known in pharmaceutical arts that derivatives and analogs of a useful molecule may have similar properties, may be more or less readily or rapidly absorbed, may be more or less stable, may have greater or fewer side effects, and the like. The U.S. Pat. Nos. 4,426,324 and 4,428,938 therefore claim not only the particular peptides disclosed but also their salts, amides, lower alkyl esters, and/or protected derivatives. Essentially, these other forms of the peptide may be regarded as equivalents or potential equivalents, and are therefore appropriately considered to be comprehended within the scope of the discovery of the pharmaceutical activity of the peptide.

As suggested by the U.S. Pat. No. 4,426,324 pharmaceutically suitable salts include those of Na, K, strong organic bases such as guanidine, and also counter ions may be included in the preparation, such as Cl—, Br—, $SO_4$—, $HPO_4$—, maleate, and ascorbate. These may be prepared by conventional means. Also, protected derivatives of a peptide may be prepared by the processes described in the U.S. Pat. No. 4,428,938. The specific processes of preparing these related forms of the TGG peptide are conventional, and the inventor does not consider them the main aspect of the instant invention, although no one would have hitherto been motivated to produce such derivatives because there would be no reason to do so unless and until one knew of a useful property thereof—here, the previously undiscovered immunomodulatory utility of the TGG peptide.

In addition, the inventor has discovered that a TGG-derivative naturally occurring in the human body (in the presence of other products, and not in purified form substantially free of other substances) has human immunomodulatory effects. As indicated above, the inventor previously discovered and disclosed in the U.S. Pat. No. 4,468,319 and U.S. application Ser. No. 643,724 that certain immunoamplifiers can be extracted from human leukocyte dialysates. By means of further extraction procedures and amino acid sequencing tests, the inventor has now ascertained that Amplifier Beta of the U.S. application Ser. No. 643,724 contains as an active immunoamplifying factor, hereinafter referred to as "Molecule Z," a molecule that is a TGG tripeptide with additional non-amino acid groups bound to it. From the apparent properties of Molecule Z, it appears to be TGG bound to a sugar, possibly a pentose sugar such as ribose—$HOCH_2(CHOH)_3CHO$—and probably not as heavy a sugar as sucrose. However, Molecule Z could be TGG bound to something simpler than ribose, such as an acetyl group, or could be an ester of TGG. Molecule Z could also be an alternative isomeric form of TGG. Although the exact structure of Molecule Z is still unascertained, it is possible to describe how to obtain it and it is believed that further work in this field (such as use of mass spectroscopy) will lead to the precise specification of the structure of the molecule. Since it is possible at this time to specify how to make Molecule Z and how to use it, it is considered that Molecule Z is within the scope of the instant invention.

EXAMPLE 2—PREPARATION OF MOLECULE Z

Amplifier Beta material was prepared and passed through the water/ethanol HPLC gradient described in the U.S. Pat. No. 4,468,379. A Perkin-Elmer Prep octadecylsilane (ODS) column was used, 6 ml/min flow rate, 25° C., and the water and ethanol solvents used were filtered and purged with helium for 20 min. The following linear gradients were used:

| Time  | % Ethanol | to % Water |
|-------|-----------|------------|
| Init. | 0         | 100        |
| 30    | 50        | 50         |
| 35    | 0         | 100        |

A fraction designated SP-1 was recovered at approximately 15.8 to 16.0 min. The SP-1 fraction was then injected into a Zorbax (DuPont) ODS HPLC column, 1 ml/min flow rate, 25° C. The solvent system was (1) 100% $CH_3CN$, ACS Reagent Grade, and (2) 0.05% trifluoroacetic acid aqueous solution, ACS Reagent Grade, pH 2.5. The following linear gradients were used:

| Time segment | Cumulative time | % CH$_3$CN |
|---|---|---|
| 0 | 0 | 0 |
| 15 | 15 | 6 |
| 30 | 45 | 40 |
| 5 | 50 | 0 |
| 1 | 51 | 0 |
| 1 | 52 | 0 |

The fraction designated herein as Molecule Z eluted at approximately 24.2 to 24.6 min. It was lyophilized and reconstituted in normal saline, and set aside for further use. The product of the above procedure was approximately 100 micrograms of Molecule Z in 100 microliters of saline.

The following HPLC procedure was used to compare the properties of TGG and Molecule Z. The data indicates that Molecule Z is TGG plus additional atoms. That is, since the TGG came out earlier on the gradient, it may be presumed that Molecule Z is a larger molecule, such as TGG bound to something additional.

EXAMPLE 3—HPLC COMPARASION TGG/MOLECULE Z 5 micrograms of TGG of Example 1 and approximately the same amount of Molecule Z of Example 2 were mixed together and injected into the HPLC column of Example 1. The same solvent and gradient system was then used.

The elution curve absorbance at 210 A (0.05 O.D. units fall scale) showed two sharp and narrow peaks, much higher than any other peaks, at approximately 21.03 and 22.65 min. The first is associated with TGG and the second with Molecule Z.

The following amino acid sequencing procedure was carried out to determine whether Molecule Z might be bound to additional amino acids. That is, the inventor desired to ascertain whether instead of Molecule Z being merely TGG with a minor modification, such as acetylation or esterification, or TGG bound to a simple group such as ribose, it was perhaps a tetrapeptide or pentapeptide. The amino acid sequencing data indicated, however, no significant amino acids but T-G-G.

EXAMPLE 4—AMINO ACID SEQUENCE DETERMINATION OF MOLECULE Z

Approximately 950 pM of Molecule Z were loaded onto the Biobrene containing filter of an Applied Biosystems Gas Phase Sequence Analyzer. The PTH-amino acids were analyzed using a Waters Model 840 HPLC. Separations were achieved on an IBM cyano column, eluted with a gradient of 0.045M Na Ac in 5% aqueous solution of tetrahydrofuran, pH 5.0, and 100% acetonitrile, at a column temperature of 40° C. The identification and quantitation of PTH amino acids were done by the PTH amino acid standards obtained from Pierce Chemical Co.; DMPTU and DPTU were also included in the standards.

The first residue was Tyr. DMPTU came off at approximately 10 min, Tyr at approximately 15.4–15.6 min, and DPTU at approximately 16.5 min.

The second residue was Gly, which came off immediately after DMPTU. DMPTU came off at approximately 9.6 min, Gly approximately 10.1 min, and DPTU at approximately 16.7 min.

The third residue was approximately the same: DMPTU, approximately 9.5 min; Gly approximately 10.1 min; DPTU, approximately 16.7 min.

The system also showed small amounts of Ile and Lys artifacts, which can be disregarded.

The sequencing data thus indicates that Molecule Z is TGG plus other groups, but that there are no other amino acids in Molecule Z. The ratio of Tyr and Gly recovered was 1:2, indicating one T molecule and two G molecules in the peptide, and no other amino acids, as shown not only by the foregoing sequence data but also by independent amino acid composition analysis. The aforementioned sequence and independent amino acid composition data for Molecule Z amino acid content were consistent, in that both indicated the presence of one T and two G molecules in the peptide.

In vivo tests of Molecule Z, parallel to those of Table I, were performed to establish its immunoregulatory power in human test subjects.

EXAMPLE 5—MOLECULE Z SKIN TESTS

The tetanus toxoid skin tests of Section II, supra, were repeated with Molecule Z. Results (mm×mm) are shown in Table 3, for two normal adult male test subjects.

TABLE 3

| Dermal reaction to antigen, with and without Molecule Z | | | | |
|---|---|---|---|---|
| Subj. #1 Prep. | Conc. | 5 hrs. | 13 hrs. | 24 hrs. |
| A | $3 \times 10^{-13}$ M | 3 × 6 | 10 × 9 | 15 × 20 |
| B | $3 \times 10^{-14}$ M | 4 × 2 | 15 × 11 | 18 × 20 |
| C | $3 \times 10^{-15}$ M | 7 × 8 | 15 × 18 | 18 × 21 |
| D | $3 \times 10^{-16}$ M | 9 × 9 | 17 × 13 | 19 × 19 |
| E | saline control | 3 × 5 | 10 × 10 | 14 × 15 |
| Subj. #2 Prep. | Conc. | 6.5 hrs. | 11.5 hrs. | 24 hrs. |
| A | $3 \times 10^{-13}$ M | 4 × 4 | 6 × 9 | 22 × 19 |
| B | $3 \times 10^{-14}$ M | 3 × 5 | 12 × 11 | 25 × 27 |
| C | $3 \times 10^{-15}$ M | 4 × 4 | 9 × 10 | 22 × 19 |
| D | $3 \times 10^{-16}$ M | 3 × 4 | 6 × 9 | 16 × 18 |
| E | saline control | 2 × 2 | 5 × 4 | 14 × 20 |

It is difficult to compare in vivo potency of Molecule Z with that of TTG. The degree of immunoamplification in vivo varies from test subject to test subject, and probably varies with regard to other individual factors (such as extent of prior sensitivity and temporal variations in the same individual). The data appears to indicate that Molecule Z and TGG have comparable immunoamplifying activity. Another possible variable may be the age of the preparation. While prior tests with Amplifier Beta indicate that it can be repeatedly freeze/thawed without significant loss of activity, it appears that two cycles of freeze/thaw inactivate both TGG and Molecule Z.

Further TGG and Molecle Z tests were carried out to assay their in vitro immunoamplification properties, similar to those of Section III and Table 2. Peripheral blood lymphocytes of four normal human donors were used with PHA mitogen, in the presence of specified serial dilution of TGG and Molecule Z, respectively. The starting dilutions were 1:1000, which is approximately $3 \times 10^{-10}$M, or 300 pM. A control was used to show increase in IL-2 production as a result of mitogen stimulation in the absence of TGG/Molecule Z. In each test, 1 microgram/ml of PHA was used, except in Test 4A, where 0.5 microgram/ml of PHA was used. IL-2 production is shown below for the various dilutions, measured in an arbitrary unit.

TABLE 4

| Test | Immunoamplifier | Dilution | IL-2 Prodn. | Max. increase |
|---|---|---|---|---|
| 1 | TGG | control | 0.69 | |
| | | 1:1000 | 1.0 | |
| | | 1:2000 | 0.93 | |
| | | 1:4000 | 1.41 | |
| | | 1:8000 | 1.76 | 61% |
| | | 1:10,000 | 1.6 | |
| 2 | TGG | control | 0.90 | |
| | | 1:4000 | 0.99 | |
| | | 1:8000 | 1.06 | |
| | | 1:16,000 | 1.28 | |
| | | 1:32,000 | 1.38 | 53% |
| 3 | Molecule Z | control | 0.90 | |
| | | 1:4000 | 0.94 | |
| | | 1:8000 | 0.84 | |
| | | 1:16,000 | 1.43 | 59% |
| | | 1:32,000 | 1.23 | |
| 4A | Molecule Z | control | 1.54 | |
| | | 1:1000 | 1.74 | |
| | | 1:2000 | 2.20 | |
| | | 1:4000 | 2.13 | |
| | | 1:8000 | 2.31 | 50% |
| | | 1:16,000 | 1.40 | |
| 4B | Molecule Z | control | 3.58 | |
| | | 1:1000 | 3.85 | |
| | | 1:2000 | 4.33 | |
| | | 1:4000 | 4.01 | |
| | | 1:8000 | 4.65 | 30% |
| | | 1:16,000 | 4.54 | |

Again, the comparability of TGG and Molecule Z is difficult to determine because of the idiosyncratic factors involved. As is seen, the baseline IL-2 production is very variable.

V. Animal tests

Other work in this field suggests that TGG should affect nonhuman mammalian subjects in a manner similar to its effect on human subjects.

EXAMPLE 6—GUINEA PIG TEST

A 60 gm guinea pig is immunized by serial injections with Mycobacterium tuberculosis. When adequately immunized, the guina pig manifests a delayed hypersensitivity (DH) reaction of 12×10 mm when injected intradermally with 5 Units of Tuberculin-PPD (Aplisol, Parke Davis, Detroit, MI). Preparations A through D of TGG of Section II and Table 1, supra, are injected together with 2.5 Units of PPD, at separate sites, and a saline control Preparation E is injected at a fifth site. The following reactions are observed (mm×mm):

| Prep. | Conc. | 6 hrs. | 12 hrs. | 24 hrs. |
|---|---|---|---|---|
| A | $3 \times 10^{-13}$ M | 3 × 3 | 5 × 6 | 6 × 7 |
| B | $3 \times 10^{-14}$ M | 4 × 3 | 6 × 8 | 9 × 8 |
| C | $3 \times 10^{-15}$ M | 8 × 10 | 12 × 14 | 14 × 14 |
| D | $3 \times 10^{-16}$ M | 6 × 8 | 8 × 7 | 8 × 6 |
| E | saline | 2 × 3 | 5 × 5 | 6 × 6 |

VI. Therapeutic use of TGG and derivatives

The foregoing data indicates the value of TGG and its derivatives as a therapeutic agent for the treatment of anergy and other immune deficiency conditions, such as those described in greater detail in the U.S. Pat. No. 4,468,379 and the U.S. application Ser. No. 643,724. TGG and Molecule Z have each been shown to augment in vitro production of IL-2, which is generally considered by those in the field to be an index of immunoamplificatory utility. Furthermore, TGG and Molecule Z have each been shown to augment in vivo immune response to antigen (dermal DTH reaction), which is also generally considered by those in the field to be an index of immunoamplificatory utility. This data strongly suggests the therapeutic utility of TGG and Molecule Z in immune deficiency conditions.

In addition, Amplifier Beta, the material from which Molecule Z was extracted, has been shown to have actual in vivo amplifier effects. In as yet unpublished studies of the inventor and his co-workers, AIDS and ARC patients to whom Amplifier Beta was administered showed: (1) augmented dermal immune response to antigen; (2) increased mitogen-stimulated in vitro IL-2 production; and (3) favorable clinical results suggesting clinical efficacy, such as weight gain and lessened rates of opportunistic infection. This clinical data further supports the indication of therapeutic use of TGG and Molecule Z in treating immune deficiency.

The data set forth earlier in this application relates primarily to subcutaneous and/or intradermal administration of TGG or Molecule Z dissolved or suspended in sterile saline. However, peptides are typically administered for medical and veterinary use with organic or inorganic carriers suitable for parenteral or enteral administration. Parenteral administration may be intravenous or intramuscular, as well as subcutaneous. In addition, transdermal patch administration is appropriate. Formulations include solid lyophilizates containing carriers that do not react with peptides, e.g., hydrocarbons, dilute or concentrated suspensions, emulsions, tablets, or injectables. Moreover, pharmaceutically acceptable salts and other derivatives, as indicated above, are appropriately used.

The experience of the inventor is that the effective dosage amount for systemic human immunoamplifier purposes is, approximately, $10^6$ times the dosage for maximum dermal response. That rule of thumb plus the foregoing data suggest that an effective human dosage amount here may be approximately 300 femtomoles, or one order of magnitude more or less. That in turn suggests a dosage amount of approximately 1200 femtograms per kilogram of human body weight, or approximately 80 picograms for a 70 kg. adult, depending on the pathological condition requiring treatment, the condition of the subject, the duration of treatment, and so on. The appropriate dosage may have to be determined for each patient and it may vary through the course of treatment.

The effect of such a dosage appears to continue for approximately 10 to 14 days, so that to maintain full effectiveness the dosage should be repeated biweekly.

The following examples are intended to be illustrative of the therapeutic applications of TGG, and not as limiting the scope of the invention.

EXAMPLE 6—CHEMOTHERAPY

A patient undergoing chemotherapy has a reduced immune system response. The attending physician is concerned that the patient may become subject to opportunistic infections and desires to increase the patient's immune system activity. The patient, an adult male, weighs 70 kgm.

The physician determines a dosage amount of TGG, that in his or her medical judgment is appropriate. (For example, 80 pg every week). This dosage is injected intradermally or subcutaneously.

The patient's immune function is monitored by weekly blood tests measuring the patient's immune capability. Monthly testing by injection of a recall antigen (such as tetanus toxoid) is also carried out.

The physician monitors the patient's progress and increases or decreases the dosage, as indicated by his or her medical judgment.

EXAMPLE 7—IMMUNE DEFICIENCY TREATMENT

A patient, an adult male, with immune deficiency (such as an AIDS or ARC patient), displays reduced function of his immune system. The attending physician is concerned that the patient may become subject to opportunistic infections and desires to increase the patient's immune system activity.

The physician determines a dosage amount that in his or her medical judgment is appropriate. (For example, 300 pg every week). This dosage is injected intradermally or subcutaneously.

The patient's immune function is monitored by weekly blood tests measuring the patient's immune capability. Monthly testing by injection of a recall antigen (such as tetanus toxoid) is also carried out.

The physician monitors the patient's progress and increases or decreases the dosage, as indicated by his or her medical judgment.

VI. Accelerated sensitivity testing

The present method for testing patients for previous exposure to tuberculosis bacillus involves injecting the patient with tuberculin and awaiting a delayed type hypersensitivity skin reaction. However, the normal response time is approximately 24–36 hours, producing an induration of approximately 18×18 mm. Hence, the patient must either come back to the clinic or doctor's office, for reexamination, or else must subsequently measure the induration and record its size on a card, which the patient has to mail back to the clinic or doctor. Unfortunately, this procedure does not lead to satisfactory results, since error and failure to return or report are common. It would therefore be very desirable to have a much faster tuberculin test, such as one that could be read within eight hours. Combining TGG or a derivative thereof with the tuberculin testing agent advantageously provides such a test.

EXAMPLE 8—TB Test

Preparation A is made up consisting of 2.5 Tuberculin Units of Purified Protein Derivative (PPD, Tuberculin-Aplisol, Parke Davis, Detroit, MI) in 0.05 ml of sterile saline, combined with 0.1 ml of sterile saline containing $3\times10^{-15}$M TGG. The total volume of 0.15 ml is injected intradermally (not subcutaneously) into a test subject shown previously to give a positive reaction to Tuberculin PPD. The following dermal reactions are observed (mm×mm):

| 5 hrs. | 8 hrs. | 24 hrs. | 48 hrs. |
|---|---|---|---|
| 18 × 20 | 16 × 18 | 16 × 18 | 7 × 6. |

Preparation B is made up consisting of 2.5 Tuberculin Units of PPD in 0.15 ml sterile saline. The total volume is injected intradermally into a test subject shown previously to be negative to Tuberculin PPD. The following dermal reactions are observed (mm×mm):

| 5 hrs. | 8 hrs. | 24 hrs. | 48 hrs. |
|---|---|---|---|
| 0 | 0 | 0 | 0 |

The same procedure may readily be adapted to histoplasmosis testing, using histoplasmin (Parke-Davis), and to other antigen-based diagnostic tests. (For histoplasmosis, the analogous preparation to Preparation A of Example 8 combines 0.05 ml of Histoplasmin ,ntigen USP (Parke Davis, 1:100 dilution) with the same amount of TGG as above.)

Moreover, the same method of delivery of the product as is now used may be used for the improved version of the diagnostic reagent. At present, tuberculin, histoplasmin, and other such reagents are distributed in individual vials containing a sufficient dosage amount for testing a patient. An appropriate amount of TGG (or TGG derivative) may be included in such vials, in order to realize the accelerated response that TGG causes. It may be desirable to include, also, a pharmaceutically acceptable stabilizing agent to extend shelf life.

GENERAL CONCLUDING REMARKS

The above described procedures disclose what the inventor beleves is a unique and hitherto uriknown method of modifying human or animal immune system response. The disclosure also described hitherto unknown compositions for effecting such immunomodulation, as well as novel extraction procedures for obtaining the desired material in medically acceptable form.

While the invention has been described primarily in connection with a specific and preferred embodiments thereof, it will be understood that it is capable of further modifications without departing from the spirit and scope of the invention. This application is intended to cover all variations, uses, or adaptations of the invention, following, in general, the principles of the invention and including such departures from the present disclosure as come within known or customary practice within the art to which the invention pertains, or as are obvious to persons skilled in the art, at the time the departure is made.

As used hereinafter and in the claims, dilute trifluoroacetic acid aqueous solution means approximately 0.05% (W/V) trifluoroacetic acid concentration.

"TGG-compound" means a peptide product comprising Tyr and Gly amino acid residues and no other amino acid residues, wherein said peptide product is no longer than a tripeptide, and wherein said peptide product may be in the form of its pharmaceutically acceptable salts, amides, esters, and protected derivatives, and may be bound to ribose or another pharmaceutical acceptable sugar having fewer than 12 carbon atoms.

"Molecule Z" means a product essentially containing TG and TGG, mixed or complexed together. It should be noted that Molecule Z, like TGG, falls within the definition of TGG-compound, as defined in the preceding paragraph.

I claim:

1. A composition for stimulating the immune system comprising an effective amount of TGG compound or molecule Z with a pharmaceutically acceptable carrier.

2. The composition of claim 1 wherein said TGG-compound is TGG.

3. The composition of claim 1 wherein said TGG-compound is selected from the group consisting of pharmaceutically acceptable salts, amides, lower alkyl esters, and protected derivatives of TGG.

4. The composition of claim 1 wherein said TGG-compound is TGG bound to a sugar having fewer than 12 carbon atoms.

5. The composition of claim 1 wherein said TGG-compound is TGG bound to at least one acetyl group.

6. The composition of claim 1 wherein said TGG-compound is Molecule Z.

7. A method of modulating the immune response of a human or animal body to antigens, comprising administering to said body the composition of claim 1.

8. The method of claim 7 wherein said modulation of immune response is amplification thereof.

9. The method of claim 8, wherein the body is a human body.

10. The method of claim 8 wherein the body is a mammalian body.

11. The method of claim 8 wherein a said antigen is an antigen to which said body has previously been exposed.

12. A method of increasing the speed or magnitude of a human being's immune response to antigens, comprising administering to said human being an effective dosage amount of TGG-compound.

13. The method of claim 12 wherein the TGG-compound is TGG or a pharmaceutically acceptable salt thereof.

14. The method of claim 12 wherein the TGG-compound is Molecule Z.

15. The method of claim 12 wherein there is concurrently administered to said human being an effective dosage amount of a diagnostic antigen.

16. The method of claim 15 wherein said antigen is tuberculin.

17. The method of claim 15 wherein said antigen is histoplasmin.

18. The composition of claim 1 wherein there is included an effective dosage amount of a diagnostic antigen.

19. The composition of claim 18 wherein the antigen is tuberculin.

20. The composition of claim 18 wherein the antigen is histoplasmin.

21. A vial comprising an effective dosage amount of TGG and an effective dosage amount of tuberculin, in a pharmaceutically acceptable liquid carrier, whereby there is provided a diagnostic reagent for testing for tuberculosis bacillus exposure.

22. A vial comprising an effective dosage amount of TGG and an effective dosage amount of histoplasmin, in a pharmaceutically acceptable liquid carrier, whereby there is provided a diagnostic reagent for testing for histoplasmosis fungus exposure.

* * * * *